(12) United States Patent
Elliott (10) Patent No.: US 6,712,843 B2
(45) Date of Patent: Mar. 30, 2004

(54) STENT WITH DIFFERENTIAL LENGTHENING/SHORTENING MEMBERS

(75) Inventor: Christopher J. Elliott, Hopkinton, MA (US)

(73) Assignee: SciMed Life Systems, Inc, Maple Grove, MN (US)

( * ) Notice: Subject to any disclaimer, the term of this patent is extended or adjusted under 35 U.S.C. 154(b) by 0 days.

(21) Appl. No.: 09/683,119

(22) Filed: Nov. 20, 2001

(65) Prior Publication Data

US 2003/0097171 A1 May 22, 2003

(51) Int. Cl.⁷ .................................................. A61F 2/06
(52) U.S. Cl. ...................... 623/1.15; 623/1.16; 623/1.53
(58) Field of Search ................................ 623/1.15, 1.44, 623/1.53, 1.17; 606/198, 191–197

(56) References Cited

U.S. PATENT DOCUMENTS

| | | | | |
|---|---|---|---|---|
| 5,383,892 A | * | 1/1995 | Cardon et al. | 623/1.16 |
| 5,817,126 A | * | 10/1998 | Imran | 623/1.15 |
| 5,855,600 A | * | 1/1999 | Alt | 623/1.15 |
| 5,957,974 A | * | 9/1999 | Thompson et al. | 623/1.13 |
| 6,026,814 A | | 2/2000 | LaFontaine et al. | |
| 6,027,529 A | * | 2/2000 | Roychowdhury et al. | 623/1.53 |
| 6,033,433 A | | 3/2000 | Ehr et al. | 623/1 |
| 6,168,621 B1 | | 1/2001 | Vrba | 623/1.2 |
| 6,290,720 B1 | | 9/2001 | Khosravi et al. | 623/1.13 |
| 6,299,636 B1 | * | 10/2001 | Schmitt et al. | |
| 6,325,820 B1 | * | 12/2001 | Khosravi et al. | 623/1.13 |
| 6,348,066 B1 | * | 2/2002 | Pinchuk et al. | 623/1.16 |
| 6,379,379 B1 | * | 4/2002 | Wang | 623/1.15 |
| 6,383,171 B1 | * | 5/2002 | Gifford et al. | |
| 6,464,719 B2 | * | 10/2002 | Jayaraman | 623/1.13 |
| 2002/0198588 A1 | | 12/2002 | Armstrong et al. | |
| 2003/0158594 | * | 8/2003 | Kang et al. | |

FOREIGN PATENT DOCUMENTS

| | | |
|---|---|---|
| WO | 98/47447 | 10/1998 |
| WO | 01/35864 | 5/2001 |

OTHER PUBLICATIONS

U.S. patent application Ser. No. 08/511076, filed Aug. 3, 1995, Brown et al.

* cited by examiner

*Primary Examiner*—David O. Reip
(74) *Attorney, Agent, or Firm*—Vidas, Arrett & Steinkraus, P.A.

(57) ABSTRACT

A stent includes a first portion which does not substantially lengthen axially upon radial contraction of the first portion and a second portion which lengthens axially upon radial contraction of the second portion. The second portion extends from the first portion and constitutes a free end portion of the stent.

22 Claims, 7 Drawing Sheets

STENT WITH DIFFERENTIAL LENGTHENING/SHORTENING MEMBERS

BACKGROUND OF INVENTION

Stents are used for a variety of medical purposes in the body including in the coronary arteries, the peripheral arteries, arteries of the neck, cerebral arteries, veins, biliary ducts, urethras, ureters, fallopian tubes, bronchial tubes, the trachea, the esophagus and the prostate. Stents are typically placed or implanted within a bodily vessel, for example, for treating stenoses, strictures or aneurysms therein. They are implanted to reinforce collapsing, partially occluded, weakened, or dilated sections of a blood vessel.

Stents may be self-expanding, mechanically expandable or hybrids. Examples of self-expanding stents include coil stents and stents made from shape memory materials such as nitinol. One such stent is disclosed in copending, commonly assigned U.S. application Ser. No. 08/511,076. Mechanically expandable stents are most often expanded by medical balloons. Such stents are typically made of metals such as stainless steel. An example of the latter is disclosed in U.S. Pat. No. 6,033,433. Hybrid stents may be mechanically expandable in part and self-expanding in part. An example of such a stent is disclosed in copending, commonly assigned U.S. Pat. No. 6,168,621.

Figure 1:
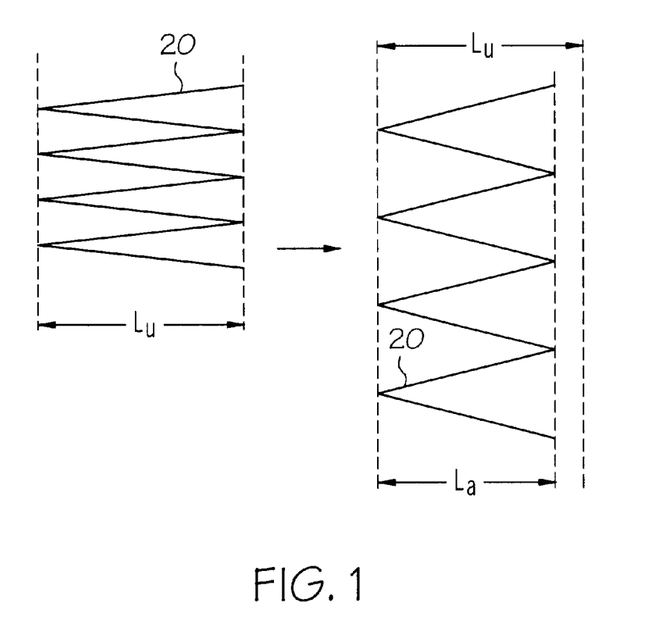
FIG. 1 shows a schematic drawing of a serpentine portion of a stent prior to expansion and after expansion.
Figure 2:
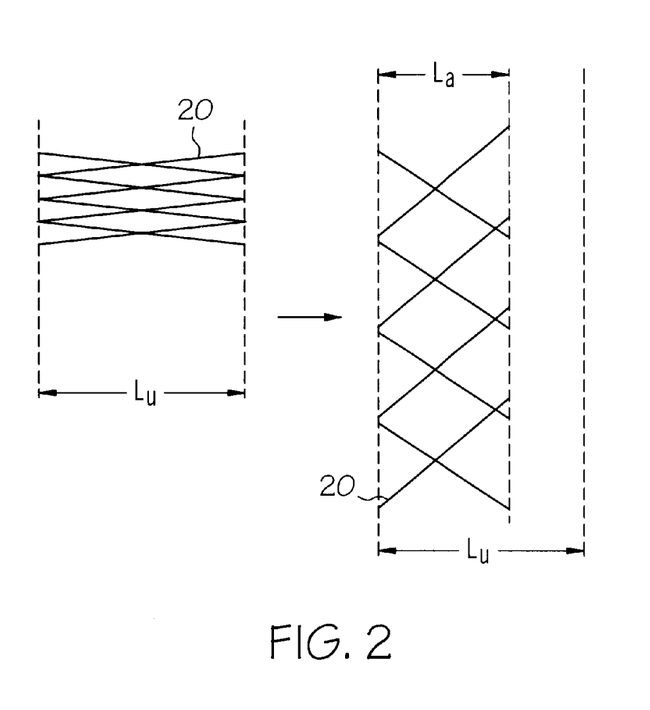
FIG. 2 shows a schematic drawing of a portion of a braided stent prior to expansion and after expansion.

Many of the stents known in the art have a tendency to shorten to varying degrees upon radial expansion of the stent. Braided stents, for example, tend to shorten axially upon radial expansion to a greater extent than many of the tubular stents having serpentine structures. As shown in FIG. 1, serpentine segment with struts 20 is shown having a unexpanded length $L_u$ slightly longer than the expanded length $L_e$ of the segment whereas braided segment with struts 20 is shown having a unexpanded length $L_u$ much longer than the expanded length $L_e$ of the segment.

Conversely, braided stents, upon the application of a compressive force thereto have a tendency to lengthen to a much greater extent than tubular stents having serpentine structures.

When a tubular stent with a serpentine structure is subjected to a compressive force, resistance to the compressive force will come largely from the radial direction. Typical methods of increasing the resistance to compressive forces involve increasing the width of the struts of the stent or the wall thickness. The use of wider struts or thicker walls may lead to less flexible stent designs or increases in the profile of the stent.

Unlike a tubular stent having a serpentine structure, when a braided stent is subjected to a compressive force, resistance to the compressive force will come mainly from the axial direction as a result of the greater axial forces transmitted to the vessel wall as the stent attempts to elongate.

There remains a need for stents which are capable of providing adequate support and which are capable of being subjected to significant compressive forces. This need is particularly felt in stenting arteries of the neck and other vessel which are more likely to be subjected to compressive forces.

Without limiting the scope of the invention, a brief summary of the invention is set forth below. Additional details of the summarized embodiments of the invention and/or additional embodiments of the invention may be found in the Detailed Description of the Invention below. A brief abstract of certain aspects of the technical disclosure in the specification is provided as well for the purposes of complying with 37 C.F.R. 1.72.

All US patents and applications and all other published documents mentioned anywhere in this application are incorporated herein by reference in their entirety.

SUMMARY OF INVENTION

In one embodiment, the invention is directed to a stent comprising a first portion which does not substantially lengthen axially upon radial contraction of the first portion and a second portion which lengthens axially upon radial contraction of the second portion. The second portion extends from the first portion and constitutes a free end portion of the stent.

The stent may optionally comprise a third portion which expands axially upon radial contraction of the stent. The third portion, where present, constitutes another free end portion of the stent.

Typically, the first portion is in the form of a tube with openings therein. The tube with openings therein may be made via any suitable technique including by cutting openings in an already existing tube or cutting openings in a sheet and rolling the sheet into a tube. The second portion is typically braided. Where present, the third portion will also typically be braided.

Desirably, the first portion of the stent will have a delivery configuration and an expanded configuration and will foreshorten by less than 10% upon expansion from the delivery configuration to the expanded configuration. Also desirably, the second portion will foreshorten axially by an amount in excess of 10% upon expansion from the delivery configuration to the expanded configuration.

The inventive stents disclosed herein may be made of a single piece of material or of a plurality of pieces of material.

The invention is also directed to a stent having a braided first free end portion and a non-braided portion adjacent thereto. Typically, the non-braided portion will be in the form of a tube having openings therein and may be formed as described above. The braided portion may have any number of braided strands. Desirably, the braided portion comprises no more than 10 braided strands. More desirably, the braided portion comprises no more than 8 braided strands.

The braided portion and the non-braided portion may be made of one piece construction or may be joined together via any suitable technique including welding and the use of adhesives.

The inventive stent may further comprise a braided second free end portion adjacent to the non-braided portion.

The invention is further directed to a non-braided outer stent having at least one braided inner portion joined thereto. In one embodiment, the stent has a single braided inner portion. In another embodiment, the stent comprises at least two braided inner portions, including one braided inner portion at a first end of the stent and another braided inner portion at a second end of the stent. Desirably, one of the braided inner portions extends outward in an axial direction from one end of the non-braided outer stent and the other of the braided inner portions extends outward in an axial direction from another end of the non-braided outer stent.

In yet another embodiment, the invention is directed to a method of forming a stent comprising the steps of providing a tube having a plurality of strands extending therefrom, and forming a braided portion with a flowpath therethrough by braiding the strands. Desirably, the braided portion comprises no more than 10 braided strands and more desirably, no more than 8 braided strands.

The inventive method may further comprise the steps of providing a tube and removing material from at least one end of the tube to form a plurality of strands extending from the tube.

In yet another embodiment, the invention is directed to a method of stenting a peripheral vessel comprising the steps of providing any of the inventive stents disclosed herein, delivering the stent to a desired location in a peripheral vessel and radially expanding the stent at the desired location in the peripheral vessel.

The invention is also directed to stents made in accordance with any of the inventive methods disclosed herein.

Additional details and/or embodiments of the invention are discussed below.

DETAILED DESCRIPTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 3:
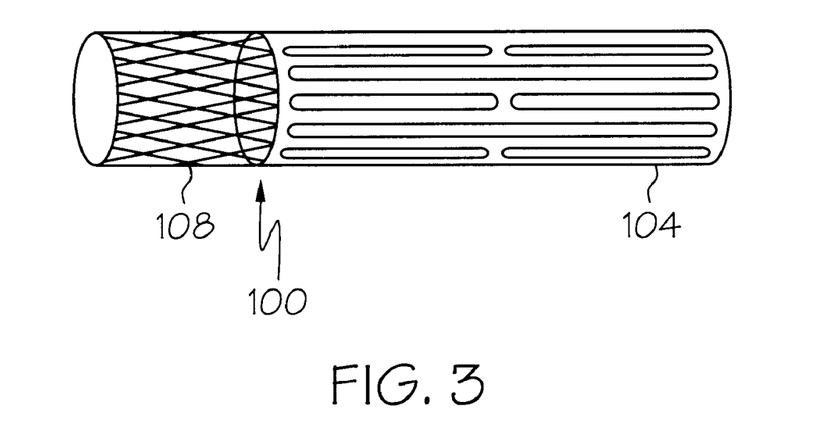
FIGS. 3–6 show side views of inventive stents.

In one embodiment, as shown in FIG. 3, the invention is directed to a stent, shown generally at 100, comprising a first portion 104 which does not substantially lengthen axially upon radial contraction of the first portion and a second portion 108 which lengthens axially upon radial contraction of the second portion. Second portion 108 extends from the first portion and forms a free end portion of the stent.

Figure 4:
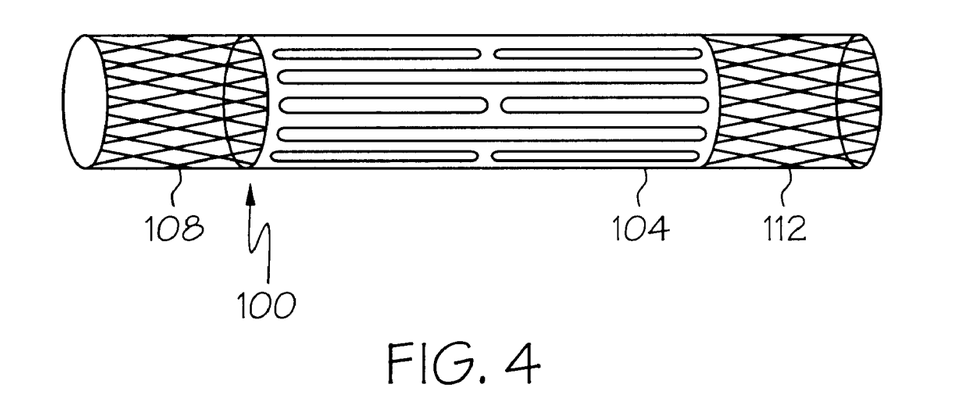

As shown in FIG. 4, in another embodiment of the invention, stent 100 comprises a third portion 112 which expands axially upon radial contraction of the stent. Third portion 112 forms another free end portion of the stent.

Figure 5:
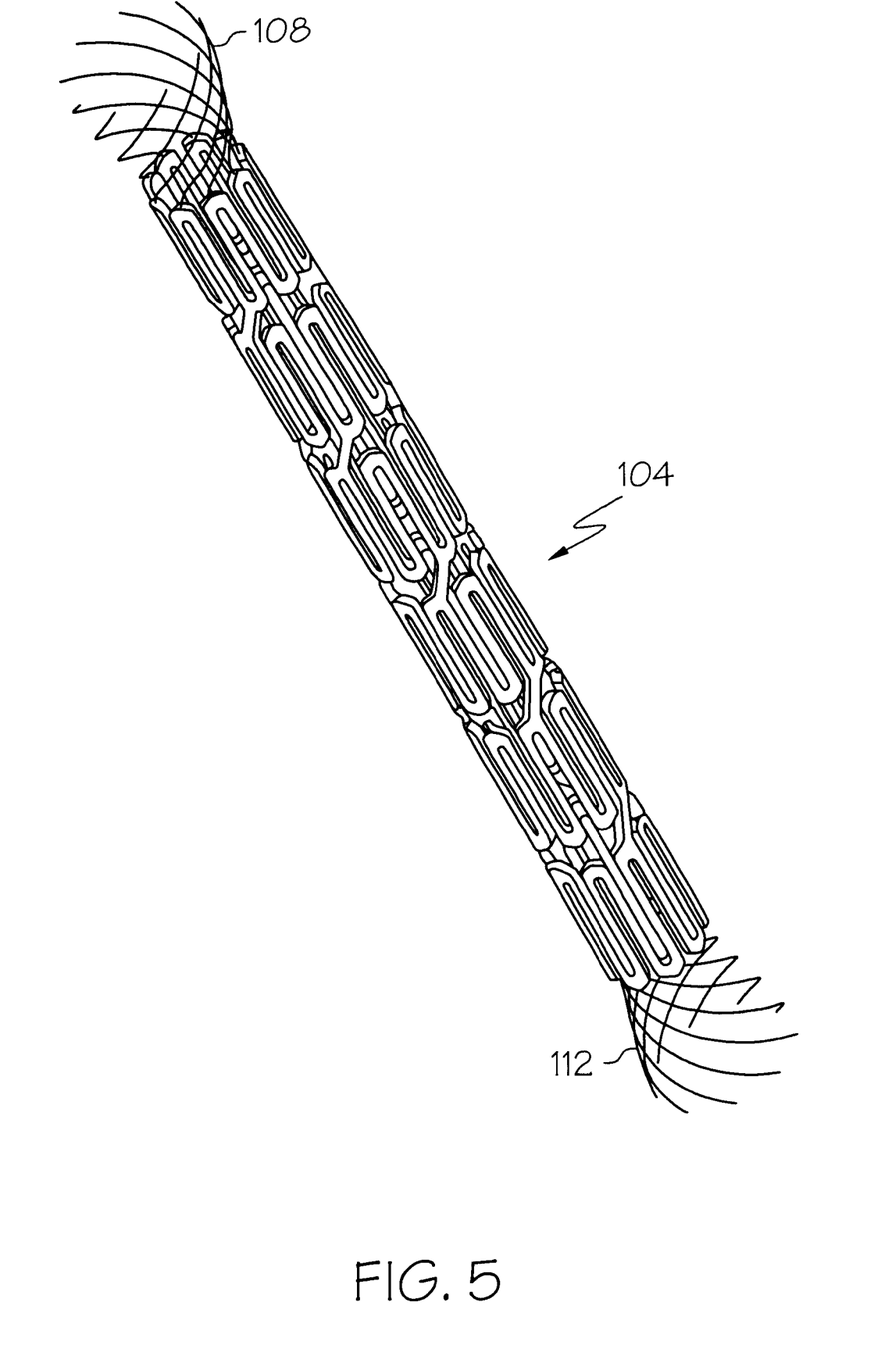
Figure 6:
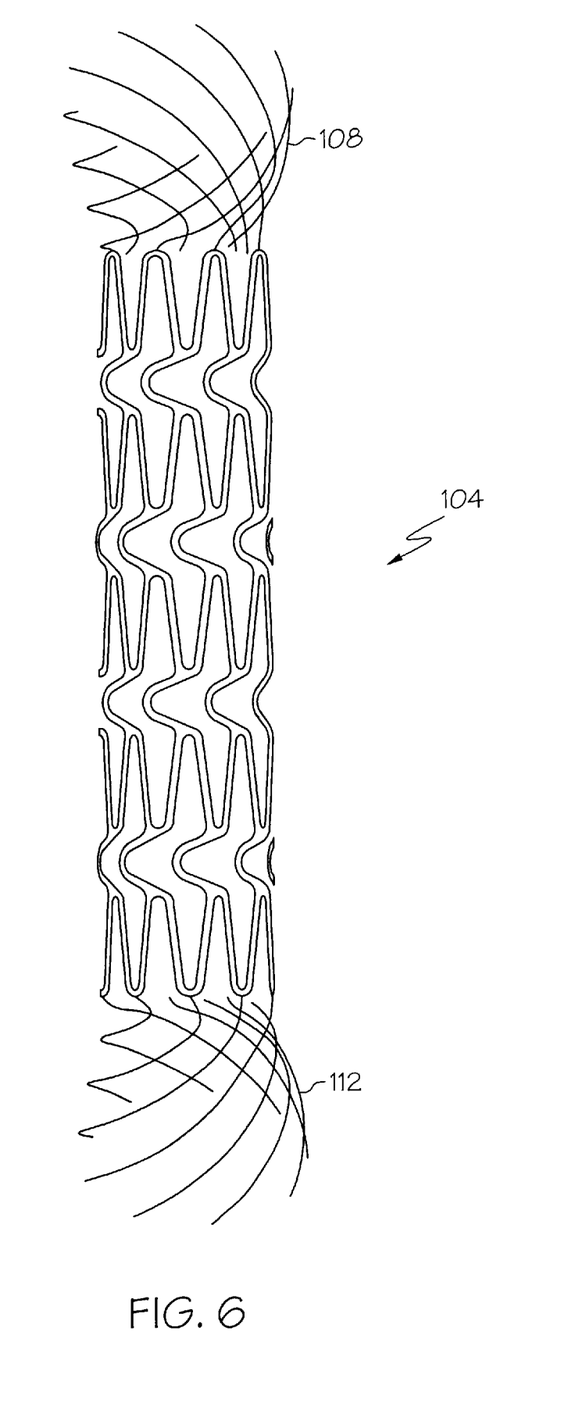

Typically, the first portion is in the form of a tube with openings therein as shown in FIGS. 3 and 4. The tube with openings therein may be of any suitable design and made via any suitable techniques including by cutting openings in an already existing tube or cutting openings in a sheet and rolling the sheet into a tube. By way of example only, other suitable designs for the stent in general and the first portion of the stent in particular are shown at 104 in FIGS. 5 and 6. In most stent types, the first portion 104 of the stent is substantially longer than the second portion 108 and optionally, where present, the third portion 112 of the stent, such as is shown in FIG. 5. This however, may not be the case where the stent 100 is or includes a side branch. Where the stent has both second and third portions, the second and third portions may be of the same length, as shown in FIG. 3 or may be of different lengths, as shown in FIGS. 4 and 5. The second and third portions may have the same number of filaments or, as shown in FIG. 6, the second portion may have a different number of filaments than the third portion. Many other configurations may also be used for the first portion of the stent. Desirably, the first portion of the stent will have a delivery configuration and an expanded configuration and will foreshorten by less than 10% upon expansion from the delivery configuration to the expanded configuration and will lengthen by less than 10% upon application of a radially inward force to the portion. Also desirably, the second portion will foreshorten axially by an amount in excess of 10% upon expansion from the delivery configuration to the expanded configuration and will similarly lengthen by an amount in excess of 10% upon application of a radially inward force to the portion.

The invention is also directed to a stent having a braided first free end portion and a non-braided portion adjacent thereto. Typically, the non-braided portion will be in the form of a tube having openings therein. Examples of suitable tube designs are shown above in FIGS. 3–6. The braided portion may have any number of braided strands. Desirably, the braided portion comprises no more than 10 braided strands. More desirably, the braided portion comprises no more than 8 braided strands. Embodiments having in excess of 10 braided strands are also within the scope of the invention. The inventive stent may further comprise a braided second free end portion adjacent to the non-braided portion.

Figure 7:
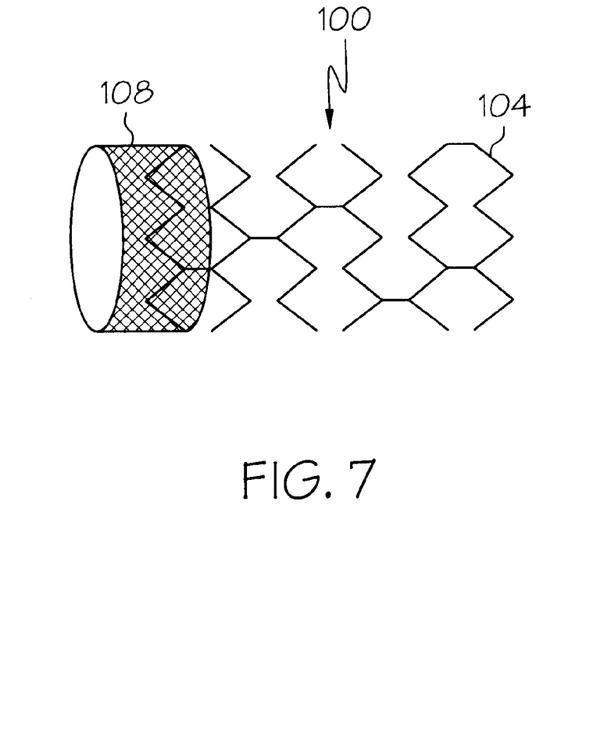
FIG. 7 shows a side view of another inventive stent.
Figure 8:
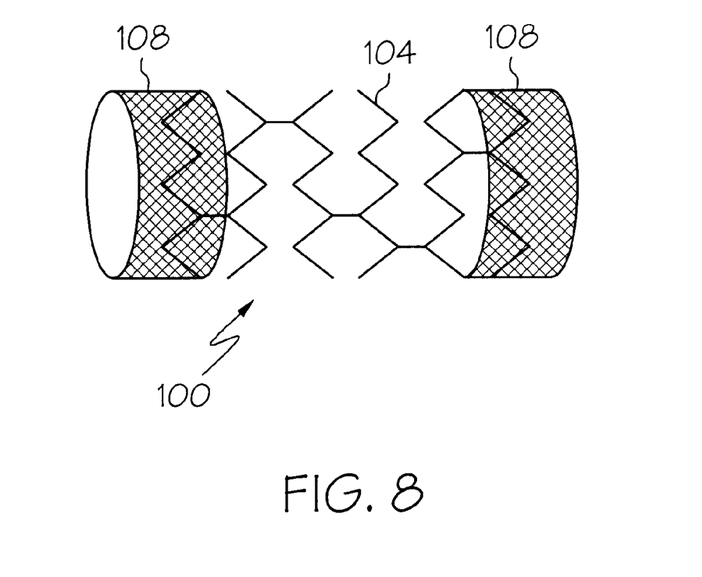
FIG. 8 shows a side view of another inventive stent.

The invention is further directed to a non-braided outer stent having at least one braided inner portion joined thereto. In one embodiment, as shown generally at 100 in FIG. 7, stent 100 has a single braided inner portion 108 which extends axially outward from the interior of end region of non-braided portion 104. In another embodiment, as shown generally at 100 in FIG. 8, the stent comprises at least two braided inner portions 108, including one braided inner portion at a first end of the stent and another braided inner portion at a second end of the stent. Desirably, one of the braided inner portions extends outward in an axial direction from one end of non-braided outer stent 104 and the other of the braided inner portion extends outward in an axial direction from another end of the non-braided outer stent. Typically, as shown in FIGS. 7 and 8, the braided inner portion will be substantially shorter than the non-braided outer portion of the stent.

Figure 9:
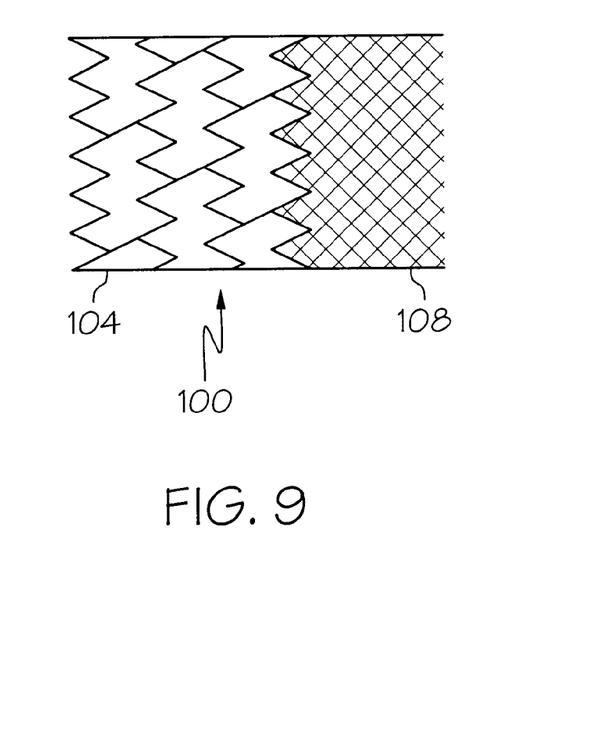
FIGS. 9 and 10 show an inventive stent before and during radial compression.
Figure 10:
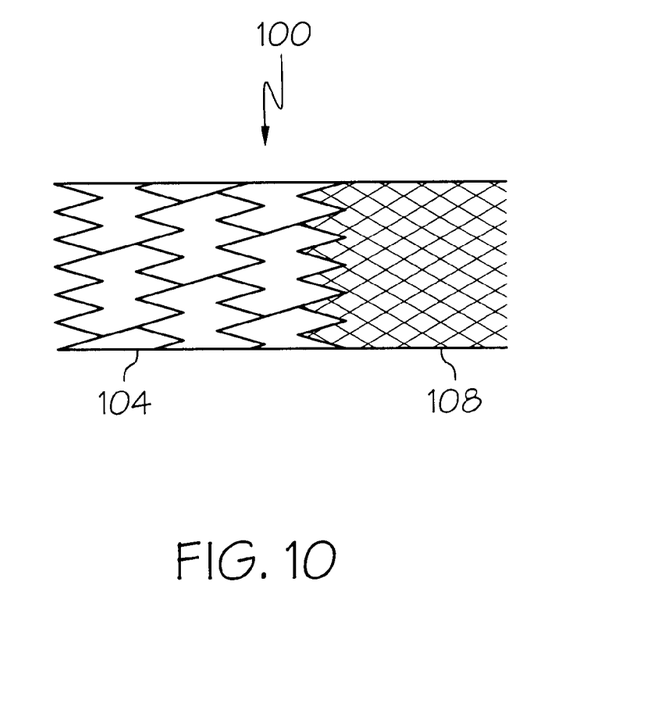
Figure 11:
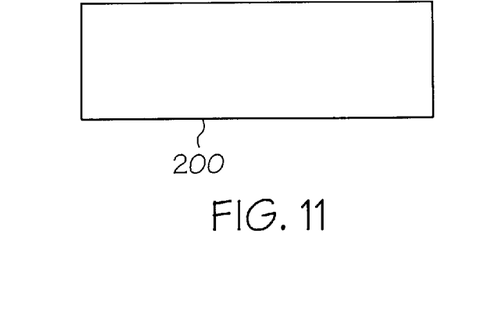
FIGS. 11–14 show an inventive stent in various stages of manufacture.
Figure 12:
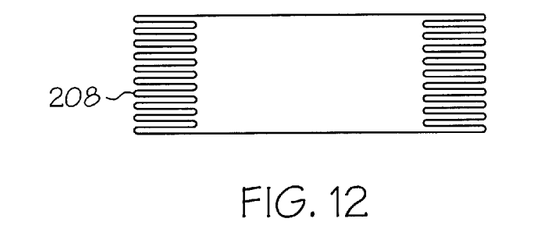

FIGS. 9 and 10 show an example of an inventive step prior to and during radial compression. During radial compression, as shown in FIG. 10, braided portion elongates in the axial direction. When such a stent is implanted in a vessel, the axial elongation of the stent will be resisted by the vessel wall thereby reducing the radial compressibility of the stent.

In another embodiment of the invention, the invention is directed to a stent having a non-braided inner portion and having at least one braided outer portion joined thereto. The braided outer portion is disposed about an end region of the non-braided inner portion and extends axially outward from the non-braided inner portion. The stent may comprise a single braided outer portion or may comprise a braided outer portion disposed about each end region of the stent. Desirably, the braided outer portion will be substantially shorter than the non-braided inner portion.

The inner and outer stents may be attached to one another via the use of adhesives, via welding or via any other suitable technique for joining materials together.

The inventive stents disclosed herein may be made of a single piece of material or of a plurality of pieces of material. In the former case, the inventive stents may be formed from a tube having a plurality of openings cut in one portion and having a plurality of strands formed in a second portion. The strands may then be braided. The openings and strands may be cut using laser techniques, chemically etched, mechanically cut, electrodischarge machined or otherwise provided in the tube. The use of laser techniques, chemical etching techniques and mechanical cutting techniques is well known in the art. Where it is desirable to have a second end portion, a tubular second end portion may be affixed to the braided portion of the stent using adhesives, welding or any other suitable technique for joining materials together.

Figure 13:
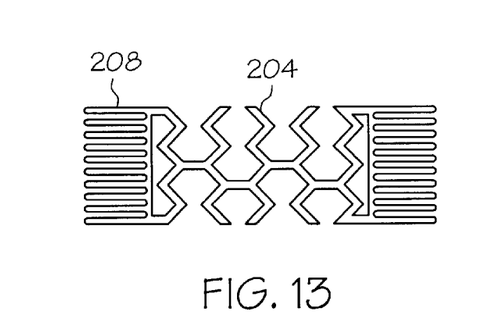
Figure 14:
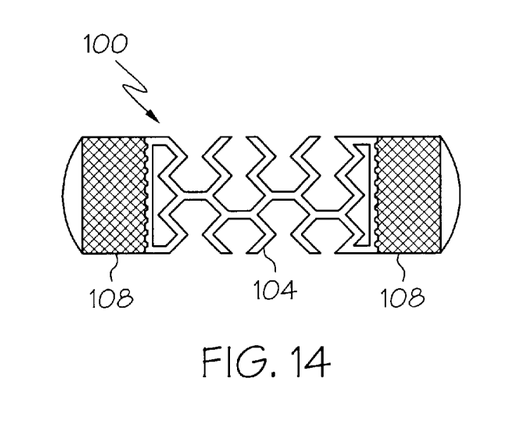

The inventive stents may also be manufactured by cutting an appropriate pattern of openings and strands in a sheet of material and rolling the sheet to form a tube. As shown in FIGS. 11–14, a sheet 200 of material is provided and a plurality of cuts made therein to form a plurality of strands 208. A desired stent pattern is then cut in the remainder of the sheet. It is also within the scope of the invention to cut the pattern and strands into the sheet in any other order. For example, the strands and openings may be cut into the sheet progressing from one end of the sheet to the other end. As shown in FIG. 13, the pattern is in the form of a plurality of interconnected serpentine segments 204. The sheet may then be rolled into a tube and the edges of the tube joined together or left unjoined to form a coil stent. The strands may then be braided, as shown in FIG. 14 to form stent 100 having braided first and second end portions 108 and a non-braided portion 104.

The invention is also directed to a method of forming a stent comprising the steps of providing a tube having a plurality of strands extending therefrom, and forming a braided portion with a flowpath therethrough by braiding the strands. Desirably, the braided portion comprises no more than 10 braided strands and more desirably, no more than 8 braided strands. The tube will typically have a plurality of openings therein.

The invention is also directed to a method of forming a stent comprising the steps of providing a tube having a plurality of openings therein and attaching thereto a braided tube. Desirably, the openings are cut in the tube and strands formed from the tube by removing material from the tube using any of the techniques disclosed herein. Also desirably, the braided tube comprises no more than 10 braided strands and more desirably, no more than 8 braided strands. The braided tube may be welded to the tube having a plurality of openings therein or may be affixed thereto via the use of adhesives or via other techniques for joining material together. Optionally, another braided portion may similarly be affixed to the other end of the tube having openings therein so that the resulting stent has two free end portions which are braided.

The braided portion(s) desirably may be attached to the outer wall surface of the first portion. It is also within the scope of the invention for the braided portion(s) to be attached to the inner wall surface of the first portion or to be attached to the end(s) of the first portion so that the first portion and the braided portion(s) are in end-to-end relationship.

The invention is also directed to stent made in accordance with any of the inventive methods disclosed herein.

The inventive stents disclosed herein may be made of any suitable stent material including metals and polymeric materials as are known in the art. Suitable metals include stainless steels, tantalum, titanium, nitinol, Elgiloy and MP35N. Portions or the entirety of the inventive stents may be radiopaque. For example, a gold coating may be provided to selected regions or the entirety of the inventive stents.

It is further within the scope of the invention for the inventive stents disclosed herein to be provided with biocompatible coatings such as lubricious coating or coatings containing therapeutic agents. Therapeutic agents include drugs and radioactive materials. Examples of therapeutic agents include antiplatelets agents, antifibrin agents, antithrombin agents and antiproliferatives. Examples of anticoagulants, antiplatelets antifibrins and antithrombins include but are not limited to sodium heparin, low molecular weight heparin, hirudin, prostacyclin and prostacyclin analogues, dextran, recombinant hirudin and thrombin inhibitor. Antiproliferative agents include angiopeptin, calcium channel blockers, colchicine, fibroblast growth factor (FGF) antagonists, fish oil, histamine antagonists, prostaglandin inhibitor, serotonin blockers, steroids, thioprotease inhibitors, PDGF antagonists, and nitric oxide.

The inventive stents disclosed herein may be used in any suitable bodily vessel including the coronary arteries, the peripheral arteries, arteries of the neck, cerebral arteries, veins, biliary ducts, urethras, ureters, fallopian tubes, bronchial tubes, the trachea, the esophagus and the prostate. Its uses include supporting vessels in the region of lesions and vessels in the region of aneurysms. It is also particularly suited for use as an intracranial stent.

The inventive stents may find particular utility in stenting a coronary artery in the region of an ostium. The braided portion of the stent may lay across the ostia and other non-diseased areas of the vessel to provide axial resistive transmission of radial compression while allowing the main body of the stent to support the diseased portion of the vessel. To that end, the invention is directed to a method of stenting comprising the steps of providing a stent comprising a portion which does not substantially lengthen upon radial compression and one or more portions which lengthen substantially upon radial compression, for example braided portions and disposing the stent across the ostium such that the braided portion lies substantially across the ostium and the portion which does not substantially lengthen lies across the diseased portion of the vessel.

The invention is also directed to methods of stenting a peripheral vessel. In one embodiment, an inventive method of stenting a peripheral vessel comprises the steps of providing any of the inventive stents disclosed herein, delivering the stent to a desired location in a peripheral vessel, and radially expanding the stent at the desired location in the peripheral vessel.

By combining the features of a tubular stent having serpentine sections with a braided stent, the braided stent serving as an anchor, it is possible to produce a stent with high constrained radial resistance, which resists axial migration and which deploys accurately.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent from claim 2; claim 5 may be taken as alternatively dependent from claims 4, 2 or 1; etc.).

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent comprising a first portion which does not substantially lengthen axially upon radial contraction of the first portion and a second portion which lengthens axially upon radial contraction of the second portion, the second portion extending from the first portion and constituting a free end portion of the stent, the first portion being a non-braided tubular member, the non-braided tubular member defining a plurality of openings therein, the second portion being braided in its entirety.

2. The stent of claim 1 wherein at least a portion of the stent is balloon expandable.

3. The stent of claim 1 wherein at least a portion of the stent is self-expanding.

4. The stent of claim 1 further comprising a third portion which expands axially upon radial contraction of the stent, the third portion constituting another free end portion of the stent.

5. The stent of claim 4 wherein the third portion is braided.

6. The stent of claim 1 wherein the first portion is formed by cutting a plurality of openings in a tube.

7. The stent of claim 1 wherein the first portion is formed of a rolled sheet with openings provided therein.

8. The stent of claim 1 having a delivery configuration and an expanded configuration wherein the first portion foreshortens by less than 10% upon expansion from the delivery configuration to the expanded configuration.

9. The stent of claim 8 wherein the second portion foreshortens axially by an amount in excess of 10% upon expansion from the delivery configuration to the expanded configuration.

10. The stent of claim 1 made of a single piece of material.

11. A non-braided outer stent having at least one braided inner portion joined thereto, the non-braided outer stent defining a plurality of openings therethrough, only a portion of the non-braided outer stent being disposed about at least a portion of the at least one braided inner portion.

12. The stent of claim 11 comprising a single braided inner portion.

13. The stent of claim 12 wherein the braided inner portion extends outward in an axial direction from one end of the non-braided outer stent.

14. The stent of claim 11 comprising two braided inner portions, one braided inner portion at a first end of the stent and the other braided inner portion at a second end of the stent.

15. The stent of claim 14 wherein one of the braided inner portions extends outward in an axial direction from one end of the non-braided outer stent and the other of the braided inner portions extends outward in an axial direction from another end of the non-braided outer stent.

16. A method of forming a stent comprising the steps of:

providing a tube, the tube being a non-braided tubular member defining a plurality of openings therethrough, the tube having a first end and a second end and a plurality of strands extending from each of the first end and second end;

forming a braided portion with a flowpath therethrough at each end of the tube by braiding the strands, each braided portion having an end corresponding to an end of the stent.

17. The method of claim 16 wherein the braided portion comprises no more than 10 braided strands.

18. The method of claim 16 wherein the braided portion comprises no more than 8 braided strands.

19. The method of claim 16 wherein the tube having the plurality of strands extending therefrom is formed of a single piece of material.

20. The method of claim 16 wherein the braided portion shortens in an axial direction by in excess of 10% upon expansion of the stent.

21. The method of claim 16 wherein the providing step further comprises the steps of:

providing a tube;

removing material from at least one end of the tube to form a plurality of strands extending from the tube.

22. A method of stenting a peripheral vessel comprising the steps of:

providing a stent as in claim 9;

delivering the stent to a desired location in a peripheral vessel;

radially expanding the stent at the desired location in the peripheral vessel.

* * * * *